(12) United States Patent
John

(10) Patent No.: US 7,527,811 B2
(45) Date of Patent: May 5, 2009

(54) **TOPICAL DEPIGMENTING FORMULATIONS COMPRISING AN EXTRACT OF *BELLIS PERENNIS***

(75) Inventor: Sabrina John, Berlin (DE)

(73) Assignee: CLR Chemisches Laboratorium Dr. Kurt Richter GmbH, Berlin (DE)

( * ) Notice: Subject to any disclaimer, the term of this patent is extended or adjusted under 35 U.S.C. 154(b) by 11 days.

(21) Appl. No.: 10/584,436

(22) PCT Filed: Dec. 23, 2003

(86) PCT No.: PCT/EP03/14851

§ 371 (c)(1),
(2), (4) Date: Jun. 22, 2006

(87) PCT Pub. No.: WO2005/063191

PCT Pub. Date: Jul. 14, 2005

(65) Prior Publication Data

US 2006/0280704 A1    Dec. 14, 2006

(51) Int. Cl.
*A61K 36/00* (2006.01)

(52) U.S. Cl. ...................... 424/725; 424/410
(58) Field of Classification Search .................. None
See application file for complete search history.

(56) References Cited

U.S. PATENT DOCUMENTS 5,164,185 A * 11/1992 Charpin et al. .............. 424/401

7,229,648 B2 * 6/2007 Dreyer ....................... 424/725

FOREIGN PATENT DOCUMENTS

| DE | 4206233 | | 3/1993 |
| DE | 4318280 | | 12/1993 |
| JP | 2001-122730 | * | 5/2001 |
| JP | 2003-002811 | * | 1/2003 |
| WO | WO99/52536 | | 10/1999 |

OTHER PUBLICATIONS http://beauty.ivillage.com/skinbody/facecare/0,,rf9x-p,00.html—accessed May 2008.*
http://www.healthatoz.com/healthatoz/Atoz/common/standard/transform.jsp?requestURI=/healthatoz/Atoz/ency/vitiligo.jsp—accessed Apr. 2008.*
English translation of JP 07025762—1995.*
Abstract of DE4206233, Mar. 4, 1993, (1 pg).
Abstract of DE431280, Dec. 16, 1993, (1 pg).
Derwent Publications XP-002293222 Abstract of JP07025762, Jan. 27, 1995 (1 pg).
Derwent Publications XP-002293178 Abstract of RU2038070, Jun. 27, 1995, (1 pg).
Grablas, et al, "Phenolic Acids in *Flores Bellidis* and *Herba Tropaeoli*," Herba Polonica, vol. 41, No. 3, 1995, pp. 111-114.

* cited by examiner

*Primary Examiner*—Susan C Hoffman
(74) *Attorney, Agent, or Firm*—Kagan Binder, PLLC

(57) ABSTRACT

The present invention pertains to topical formulations having a depigmenting effect on human skin for cosmetic and pharmaceutical use. Moreover the present invention also provides a new process for producing an extract of *Bellis perennis L.* by aqueous extraction comprising fractionation and electrolyte exchange and an extract produced by the process of the present invention.

15 Claims, 2 Drawing Sheets

Fig. 1: Whitening effect in mouse melanoma cells (B16V)
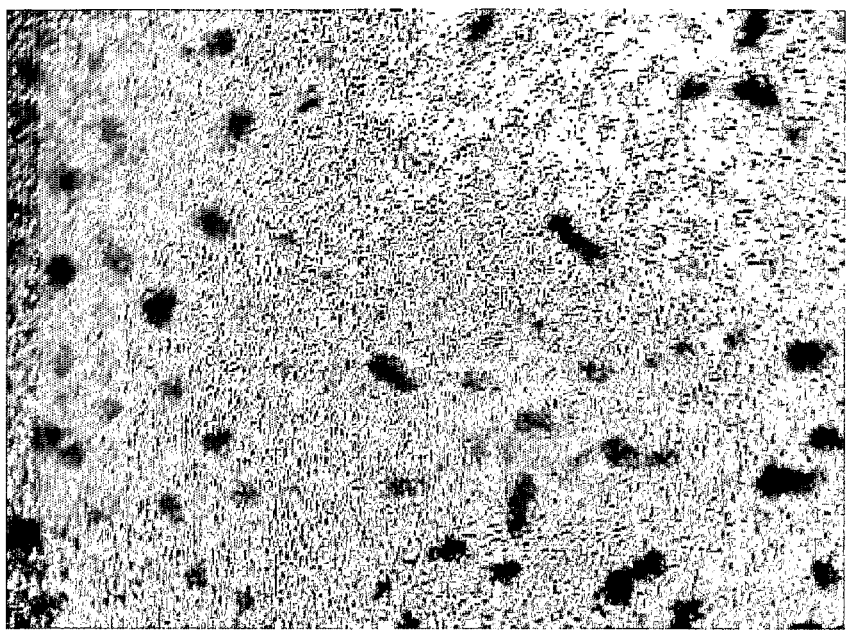
B16V mouse malanoma cells incubated with RPMI 1640 supplemented with 10% FCS = Control
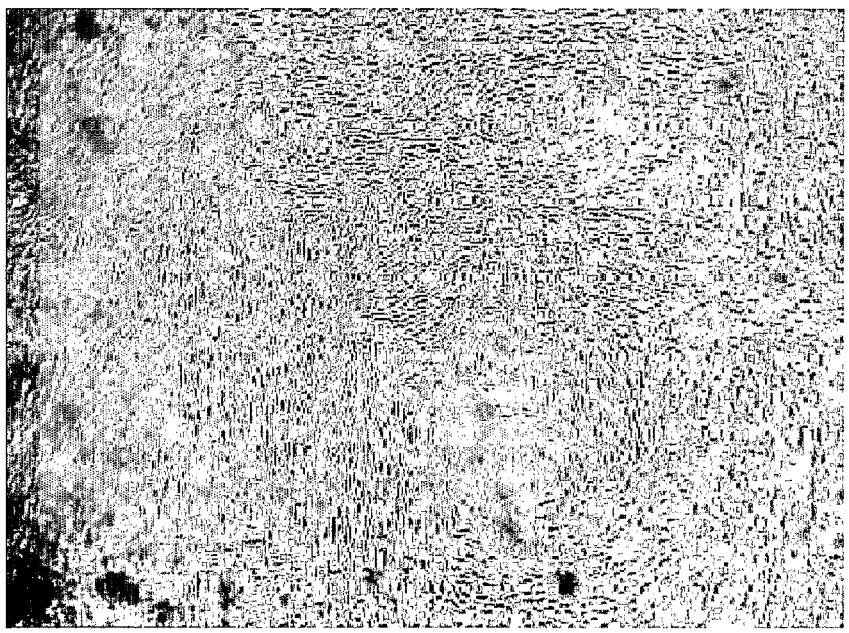
B16V mouse malanoma cells incubated with RPMI 1640 supplemented with 10% FCS and 1% Bellis Perennis

TOPICAL DEPIGMENTING FORMULATIONS COMPRISING AN EXTRACT OF *BELLIS PERENNIS*

FIELD OF THE INVENTION

The present invention pertains to topical formulations having a depigmenting effect on human skin for cosmetic and pharmaceutical use.

Moreover the present invention also provides a new process for producing an extract of *Bellis perennis L.* by aqueous extraction comprising fractionation and electrolyte exchange and an extract produced by the process of the present invention.

BACKGROUND OF THE INVENTION

*Bellis perennis L.*, commonly known as English daisy or lawn daisy belongs to the family of the Asteraceae.

It is widely used in homeopathy for treating different symptom complexes such as arthrosis, loss of appetite and sleeping disorders. Moreover *Bellis perennis L.* is also traditionally used for the treatment of dermatological problems such as acne, eczema, badly healing wounds and deeper traumata of the tissue (see e.g. H. A. Hoppe, Drogenkunde, Vol. 1, Angiospermen, 8. edt., 1975; Dr. F. Losch, Kräuterbuch; G. Leibold, Moderne Naturheilpraxis, Bassermann Verlag, 1993; M. Lange-Ernst, S. Ernst, Lexikon der Heilpflanzen, Honos Verlag; and W. D. Storl, Heilkräuter und Zauberpflanzen, AT Verlag, 2.edt., 2000).

More recently *Bellis perennis L.* has been subject of pharmacological investigations and particular ingredients, such as triterpene glycosides have been identified to exhibit a broad pharmacological activity profile such as antifungal and antimicrobial, anticancerogenic and also post ischemic neuroprotective effects (see e.g. DE 42 06 233; U.S. Pat. No. 6,444,233; G. Bader et al., Pharmazie July 1990;45(8); P.Avato et al.; Planta Med December 1997; 63(6); and C. Desevedavy et al.; Journal Nat Prod January-February 1989; 52(1)).

SUMMARY OF THE INVENTION

It has now unexpectedly been discovered that extracts of *Bellis perennis L.* have an inhibitory effect on melanogenesis and thus may be used for the depigmentation of human skin.

Melanin, which is responsible for the pigmentation of the skin, is produced in melanosomes which are localized in the melanocytes. The synthesis of melanin involves oxidative processes, whereby tyrosin is hydroxylated to dihydroxy phenylalanin (DOPA) by the enzyme tyrosinase. DOPA is then finally converted into melanin by a complex chain of oxidative reactions. Melanin accumulates in the keratinocytes of the stratum basale and reaches the surface of the skin with the keratinocytes due to continuous differentiation of the keratinocytes. The differentiated melanin containing keratinocytes form the stratum corneum as corneocytes. Oxidative processes lead to changes of the colour of melanin which becomes apparent in the individual skin pigmentation depending on skin type and other external factors. The above mentioned pigmentation process, may give rise to discoloration and in particular irregular appearing skin, which is frequently considered undesirable from a cosmetic point of view. Moreover, the process may also be subject to various pathological disorders, which have very diverse appearances.

In recent years there has been a growing demand for depigmenting cosmetical and pharmaceutical products. The irregular pigmentation pattern of acquired hyperpigmentation such as melasma (chloasma), postinflammatory melanoderma, solar lentigo, freckles (ephelides), age spots (lentigo senile), pigmentation spots that appear on the skin upon sun exposure often in conjunction with drugs such as birth control pill or other hormonal medication, or perfume, or in pregnancy is caused by various factors, including inflammation, imbalance of hormones, and some times genetic disorders. UV irradiation further aggravates these skin conditions.

The use of depigmenting (skin-lightening, skin-brightening or whitening) cosmetics and pharmaceuticals varies significantly between cultures. Whereas in Western countries it is mostly used for the prevention or treatment of the aforementioned irregular (hyper)pigmentation, in Asia and Africa skin-lightening products are also used to make the skin whiter, lighter and brighter.

In the context of the present invention it should be noted that the terms depigmenting, whitening, lightening, brightening and bleaching are used as synonyms when describing agents that are used to prevent or diminish hyperpigmentation and also undesired darker complexion.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A brief description of the drawings is as follows:

FIG. 1 is a photograph set showing whitening effect in mouse melanoma cells.

DETAILED DESCRIPTION OF PRESENTLY PREFERRED EMBODIMENTS

Figure 2:
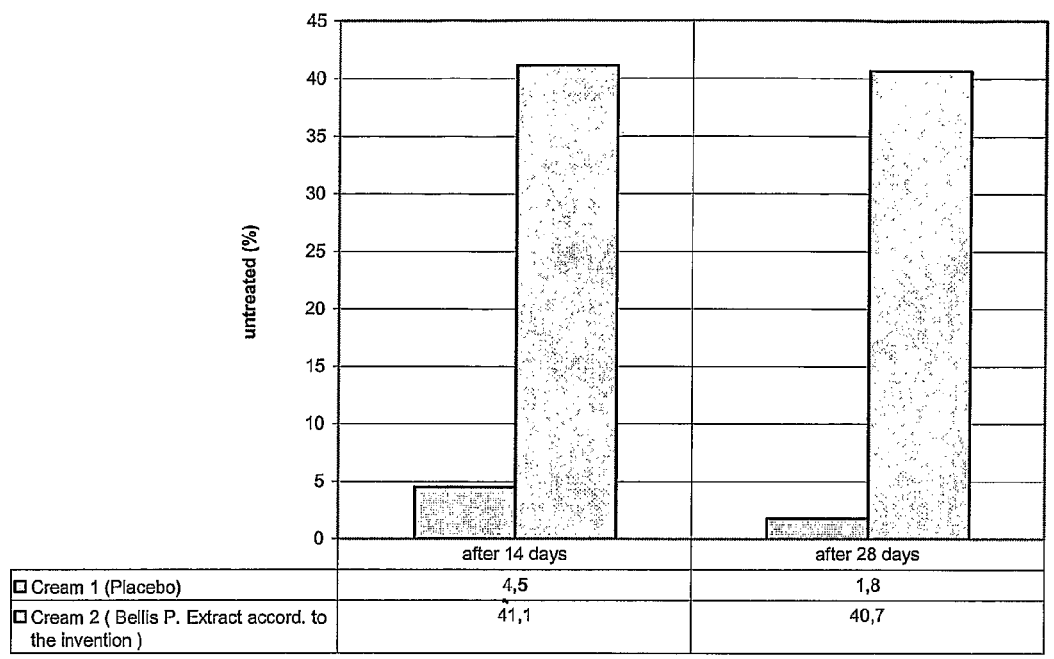
FIG. 2 is a chart showing experimental results showing depigmentation or whitening effect as compared to a placebo.

Conventional compositions which have been developed for depigmentation generally contain kojic acid, glabridin, arbutin, ellagic acid, azelaic acid, ascorbic acid and derivatives thereof, placenta extract, rucinol and hydrochinone, and plant extracts from a wide variation of plants such as wildberry, mulberry, bearberry, licorice, lemon, matricaria chamomilla, cumin seed, wolo, water cress or mixtures of any of the before mentioned.

An overview on chemical and instrumental approaches to treat hyperpigmentation is given in S. Briganti et al., Pigment Cell Res 16:101-110;2003.

Some substances that exhibit depigmenting activity cannot be used cosmetically or for pharmaceutical purposes because of their toxicity (e.g. mercury salts), of the cutaneous irritation they induce (mercapto amines, oxidizing agents like hydrogen peroxide) or because of the instability of ascorbic acid or of the reduced activity of its derivatives. Other compounds such as phenolic derivatives, corticosteroids, polyphenols, various vegetable extracts are used as components in many depigmenting preparations are now on the market. However, these compounds show side effects like hydroquinone or are very slow acting. Hydrochinone is considered to be cancerogenic, thus a legal procedure has been implemented to ban its cosmetic use in Europe.

Thus there is a growing demand for the ideal depigmenting agent which while exhibiting a potent, rapid and selective bleaching/whitening/lightening/brightening effect on hyper-activated melanocytes should not be associated with any short- or long-term side effects. Moreover the desired depigmentation agent should be stable and compatible with other cosmetic or pharmaceutical ingredients.

As used in the present invention the term hyperpigmentation refers to a localised or generalised increased melanin content of the skin, which may be acquired or inherent. Hyperpigmentation which may be treated according to the present invention include pigmented nevus, nevus spili, ephelides, lentigines, combined nevus, bathing trunk nevus, nevus systematicus, neurofibromatosis (v. Recklinghausen), Peutz-Jeghers syndrome, Albright's disease, blue nevus, Mongolian spot, nevus tardi, chloasma in particular chloasma gravidarum, or chloasma virginum peribuccale, linea fusca, Riehls melanosis, melanodermitis toxica, poikiloderma reticulata, angiodermitis pigmentosa et purpurica, post lesional hyperpignientation, phyto-photodermatoses, berloque dermatitis, Eau-de-Cologne (beloque)-pigmentation, lichen rubber or impetigo after psoriasis, incontinentia pigmenti, melanosis due to arsenic, idiopathic hemochromatosis, bronze diabetes, cirrhosis of the liver, Addison's disease, Grave's disease, melanocarcinosis, pellagra, sprue, tuberculosis, or pernicious anemia.

Moreover the pharmaceutical compositions according to the present invention may also be used for the therapy of hypopigmnentation (leucodermia) to even out the white spots. Preferred indications are thus also, naevus achromicus, naevus aenemicus, poliosis, albinoidism, vitiligo, leucoderma acquisitum Sutton, postlesional hypopigmentation such as leucoderma psoriatricum, leucoderma syphiliticum, vitiligo gravior, pinta, kwashiorkor, toxic depigmentation (e.g. due to hydrochinone or furcin), dyschromia parasitica, pityriasis versicolor alba, streptoderma alba simplex, Vogt-Koyanagi syndrome, canities praecox, Simmonds-Sheehan syndrome and Werner's syndrome.

Particularly preferred is the treatment of vitiligo, providing a better alternative to the presently used hydrochinone containing compositions which exhibit side effects.

The cosmetic compositions according to the present invention may be used for depigmnenting the human skin in case of irregular pigmentation pattern due to acquired hyperpigmentation such as melasma (chloasma); postinflammatory melanoderma; solar lentigo; freckles (ephelides); age spots (lentigo senile); pigmentation spots that appear on the skin upon sun exposure often in conjunction with drugs such as birth control pill or other hormonal medication, perfume, or in pregnancy, discoloration due to chemical peels and dermabrasion, pre-and post- laser resurfacing, or pre- and post -laser hair removal; pigmented keratosis or hypopigmentation after traumatas (scars).

Moreover they may also be used for lightening/brightening the complexion or forms of hyperpigmentation and hypopigmentation mentioned above.

As already mentioned above the present invention is based on the unexpected finding that extracts of *Bellis perennis L.* exhibit an inhibitory effect on melanogenesis. The depigmenting effect is very pronounced and has a very rapid onset.

According to the present invention any extract of *Bellis perennis L.* obtained by decoction, digestion, percolation, soxlethtation, maceration or any other appropriate method known to the person of skills in the art may be used.

Suitable extraction media and solvents are water, aqueous buffers, glycols or glycol-water mixtures, alcohols or alcohol-water mixtures, glycerin or glycerin-water mixtures. Preferred extraction media/solvents are water or aqueous buffer, ethanol ethanol-water mixtures, and methanol or methanol-water mixtures. Additionally also extracts obtained by extraction with glycols like propylene glycol, butylenes glycol or water mixtures thereof having preferably a water content of 5 to 60% may be used according to the present invention. In a preferred embodiment a sodium-citrate buffer according to Sörensen (buffer containing 0.1M disodium citrate and 0.1N HCl, having a pH between 1.2 and 5.0, preferably between 2.0 and 5.0, most preferred pH 3.0) is used. In a further preferred embodiment a phosphate buffer according to Sörensen (0.06M potassium phosphate and 0.06M disodium phosphate, pH range 5 to 8, preferably pH 5) is used.

The extracts may be prepared from fresh or dried plant material, whereby the whole plant or the flower heads of *Bellis perennis L.* may be used. The use of the flower heads is preferred.

The proportion between drug and extraction medium ranges from 1:10 to 1:200. The preferred proportion is 1:20.

A further object of the present invention is to provide a process for producing an aqueous extract of *Bellis perennis L.* and an extract obtained by that process.

The following examples are for illustrative purposes only and shall not limit the scope of the invention.

| | Extraction media | Amount of dry plant material | Temperature | Extraction time |
|---|---|---|---|---|
| Example 1 | 95% Water | 5% | 100° C. | 1 h |
| Example 2 | 95% buffer containing 0.06M potassium phosphate and 0.06M disodium phosphate, pH 5.0 | 5% | 80° C. | 12 h |
| Example 3 | 95% ethanol (70%) | 5% | 25° C. | 10 days |

According to the invention the extraction time and temperature may vary depending on the extraction media, particularly an extraction time between 1 h and 10 days is preferred, the temperature preferably may range between 25° C. and 100° C.

An particularly preferred embodiment of the present invention is an extract obtained from dried flowers by water extraction (i.e. decoction) at a temperature of 100° C. for 1 h, whereby the proportion drug: extraction medium is 1:20. The crude extract is cooled to 40° C. or below and centrifuged to separate insoluble constituents and sterile filtered (pore size: 0.2 μm). Then reverse osmosis is carried out to prevent sediment formation catalysed by electrolytes specific for *Bellis perennis L.* Then buffer, preferably citrate buffer according to Sörensen (39.9% 0.1M disodium citrate and 60.1% 0.1N HCl, pH 3.0) and a preservative, preferably 0.2% potassium sorbate, are added to the electrolyte-free extract. To prevent potential discoloration of the extract caused by high molecular components, the latter are separated by means of ultrafiltration (MW cut-off: 100 kDa).

The precise biochemical basis for the depigmenting effect of the extract of *Bellis perennis L.* is unknown. As outlined the depigmenting effect is very pronounced and rapid in onset.

In contrast to most of the presently used depigmentation or whitening agents which are potent tyrosinase inhibitors and thus can also exhibit the aforementioned side effects, the extract of *Bellis perennis L.* only shows a weak inhibition of tyrosinase.

Tyrosinase inhibition takes place in the melanosomes of the melanocytes. Therefore the inhibitor needs to pass the skin barrier, reach the melanocytes and pass the cell membrane. Depending on the molecule, this may have side effects such as cytotoxic effects.

The depigmenting activity of the extract may at least in part be due to an anti-oxidative effect, as e.g. UV-induced inflammation mediators, such as free radicals are able to stimulate melanocytes to enhanced synthesis of melanin. Contrary to ascorbic acid which is also used for depigmentation of human skin the anti-oxidative capacity of the extract of *Bellis perennis L.* is stable and does not require any particular formulation technique or derivatisation.

The *Bellis perennis L.* extract of the present invention has a distinct anti-oxidative capacity, which effectively inhibits the oxidative processes in the melanocytes and thus in consequence may reduce the synthesis of new melanin. As these processes are responsible for an enhanced pigmentation in the stratum corneum, the extract according to the present invention is effective in different layers of the skin. Thus the lightening effect is due to influencing and modulating intracellular mechanisms and not due to an external UV-filtering effect.

However, the very prominent and rapidly observable depigmenting effect of *Bellis perennis L.* cannot solely be attributed to its anti-oxidative effect, but is likely to be due to modulation of other biochemical steps involved in melanin biosynthesis. Thus its effect may also be due to its influence on endothelin. Endothelin antagonists are known to cause a four-times accelerated inhibition of the melanin synthesis, as they do not need to enter the melanosomes to inhibit the tyrosinase or the oxidative processes. Penetration into deeper layers of the epidermis is sufficient to inhibit endothelin (see Matsuda et al., Cosm Toil (10) 65-77(1996)).

The extracts may be included in common cosmetical and pharmaceutical formulations known to the person of ordinary skills in the art (see e.g. Bauer et al., Pharmazeutische Technologie, 5. edt. Govi-Verlag Frankfurt, 1997; Rudolf Voigt, Pharmazeutische Technologie, 9. edt., Deutscher Apotheker Verlag Stuttgart, 2000), such as O/W and W/O creams, O/W and W/O emulsions, gels, multiple emulsions (W/O/W and O/W/O), cosmetic dispersions (hydrodispersions and lipodispersions), sticks, formulations comprising a tenside or simple solutions (oily or aqueous).

According to the present invention the extract of *Bellis perennis L.* may be formulated also in combination with other plant extracts or chemical compounds mentioned above having a depigmenting, anti inflammatory or anti-oxidative effect.

The compositions for use according to the present invention may comprise about 1% to about 10% of *Bellis perennis* extract, a content of about 2% to 5% is preferred.

A content of about 2%, 3%, 4% or 5% is particularly preferred.

The formulation examples below are included for illustrative purposes only and shall not limit the scope of the invention.

FORMULATION EXAMPLE 1

Skin Lightening Cream (O/W)

| Phase | Tradename | INCI | Amount (w/w) |
|---|---|---|---|
| A | Tego Care PS | Cetearyl Glucoside | 4.00% |
|  | Arlamol HD | Isohexadecane | 6.00% |
|  | Tegosoft MM | Myristyl Myristate | 1.00% |
|  | Tegosoft OS | Octyl Stearate | 6.00% |
|  | Lanette O | Cetearyl Alcohol | 2.00% |
|  | Abil 350 | Dimethicone | 3.00% |
| B | Water | Aqua | 71.40% |
|  | Glycerin | Glycerin | 2.00% |

-continued

| Phase | Tradename | INCI | Amount (w/w) |
|---|---|---|---|
| C | Phenonip | Phenoxyethanol, Methylparaben, Ethylparaben, Butylparaben, Propylparaben, Isobutylparaben | 0.60% |
|  | Aerosil 200 | Silica | 1.00% |
| D | Citric acid | Citric acid | q.s. |
| E | *Bellis perennis L.* extract |  | 3.00% |

Phases A and B are heated separately to 70° C. Phase A is added to phase B, and then homogenized for 2 minutes. The homogenisate is then cooled down to 30° C. under stirring. Phase C is then added to the homogenisate and stirred to obtain a homogenous emulsion. The pH is adjusted to about pH 4.0 to 5.0 with phase D. Then phase E is added to the emulsion.

FORMULATION EXAMPLE 2

Skin Lightening Lotion (O/W)

| Phase | Ingredient | INCI | Amount (w/w) |
|---|---|---|---|
| A | Amphisol K | Potassium Cetyl Stearate | 2.00% |
|  | Myritol 318 | Caprylic/Capric Triglyceride | 4.00% |
|  | Tegosoft TN | Sucrose Stearate | 4.00% |
|  | Cetiol SN | Cetearyl Isononate | 1.00% |
|  | Tegin | Glyceryl Stearate | 3.00% |
|  | Lanette 16 | Cetyl Alcohol | 1.00% |
|  | Abil 350 | Dimethicone | 0.1% |
| B | Water | Aqua | 72.85% |
|  | Glycerin | Glycerin | 3.00% |
|  | Keltrol RD | Xanthan Gum | 0.25% |
| C | Polyglycol 400 | PEG 400 | 5.00% |
|  | Phenonip | Phenoxyethanol, Methylparaben, Ethylparaben, Butylparaben, Propylparaben, Isobutylparaben | 0.80% |
| D | *Bellis perennis L.* extract |  | 3.00% |
| E | Citric Acid | Citric Acid | q.s. |

Xanthan gum is dispersed in phase B. Phases A and B are heated separately to 75° C. Phase A is then added to phase B under stirring, followed by homogenisation. The resulting homogenisate is the cooled down to 30° C. and phases C and D are added. The pH is adjusted to about 4.5-5.0 by addition of phase E.

FORMULATION EXAMPLE 3

Skin Lightening Gel

| Phase | Ingredient | INCI | Amount (w/w) |
|---|---|---|---|
| A | Water | Aqua | 84.90% |
|  | Elfacos CD 481 | Hydroxyethylcellulose | 1.50% |
|  | Abil B 88183 | PEG/PPG-20/6 Dimethicone | 2.00% |

-continued

| Phase | Ingredient | INCI | Amount (w/w) |
|---|---|---|---|
| B | Glycerin | Glycerin | 3.00% |
|  | Phenonip | Phenoxyethanol, Methylparaben, Ethylparaben, Butylparaben, Propylparaben, Isobutylparaben | 0.60% |
| C | NaOH 10% | Sodium Hydroxide | q.s. |
|  | Citric Acid | Citric Acid | q.s. |
| D | Polyglycol 400 | PEG-400 | 5.00% |
| E | *Bellis perennis* extract |  | 3.00% |

Hydroxyethylcellulose is dispersed in water, Abil B 88183 is then added. Phase B is prepared and added to phase A. The pH is adjusted to about 8.5 with NaOH (10%) to obtain a clear gel. Then the pH is adjusted to about pH 4.0 to 5.0 with citric acid. Then phase D is added under stirring. Finally phase E is added and mixed to obtain a homogenous gel.

The extract according to the present invention did not show any cytotoxic effects in in vitro studies in human keratinocytes (HaCaT) or mouse melanoma cells (B 16V). As demonstrated in Tables 1 and 2 below the extract according the present invention did not have any cytotoxic effect and even stimulated the metabolic activity of the cells. The metabolic activity of the tested cells was tested by the MTT-test, the absorbance was measured at 570 nm.

MTT-test Principle:

The yellowish tetrazolium salt MMT is reduced to dark blue formazan through ring cleavage by mitochondrial dehydrogenase (succinate). The intensity of this color change can be measured by an ELISA reader and the obtained values (OD=optical density at 570nm) can be used as a measure for cell viability.

In the mitochondria where the dehydrogenases are localized the oxidative metabolic processes of the cells take place. This process aims at converting oxidation energy into energy rich ATP by oxidative phosphorylation. As this requires involvement of dehydrogenases, there is a direct relation between increased dehydrogenase activity, resultant enhanced metabolism and increased cellular energy potential.

Cytotoxicity Test in Mouse Melanoma Cells (B16V)

Mouse melanoma cells were grown in RPMI 1640 medium supplemented with 10% FCS, L-glutamine and gentamycine. After trypsination $5 \times 10^3$ cells were transferred into the wells of a microtiter plate. *Bellis perennis* extract containing preservatives had to be dialyzed (MW cut-off: 500 Da). Sample dilutions were filled into the proper wells with medium together with 10% FCS. As control, wells with medium plus FCS without sample dilution were used. The plate was incubated at 37° C., 5% $CO_2$ for 72 hours. 10 µl of a MTT solution (5 mg/ml) was added to the 100 µl/well. The plate was incubated at 37° C., 5% $CO_2$ for 2 hours. The supernatant was removed and a formazan redissolving solution (99.4% DMSO, 0.6 ml acetic acid, 10.0 g laurylsulfate) was added to each well. Cytotoxic or metabolic enhancing activity can be measured by reading the absorption at 570 nm in a microplate reader (MRX, Dynex).

TABLE 1

Determination of the cytotoxicity on mouse melanoma cells (B16V)

| % extract | OD 570 nm |
|---|---|
| 0 (control) | 1.48 |
| 1.00 | 1.65 |
| 1.50 | 1.66 |
| 2.00 | 1.70 |
| 2.50 | 1.65 |
| 3.00 | 1.68 |
| 3.50 | 1.69 |

Cytotoxicity Test in Human Keratinocytes (HaCaT)

Normal human keratinocytes (HaCaT) were grown in Dulbeco's Modified Eagle medium (DMEM) supplemented with 5% FCS. Prior to trypsination in stationary phase the cells were pretreated with EDTA solution. A cell suspension was prepared and seeded in microtiter plates at $3 \times 10^4$ cells/well. Then the MTT-test was carried out analogously as described above and the absorption read at 570 nm.

TABLE 2

Determination of the cytotoxicity on human keratinocytes (HaCaT)

| % extract | OD 570 nm |
|---|---|
| 0 (control) | 0.70 |
| 0.20 | 0.71 |
| 0.40 | 0.70 |
| 0.60 | 0.70 |
| 0.80 | 0.76 |
| 1.20 | 0.81 |
| 1.60 | 0.83 |
| 1.80 | 0.82 |
| 2.00 | 0.84 |

The same test was also performed with an extract according to the present invention which had been stored for 5 months at ambient temperature.

TABLE 3

Determination of the cytotoxicity on human keratinocytes (HaCaT) after 5 months storage at ambient temperature

| % extract | % OD 570 nm |
|---|---|
| 0 (control) | 100% |
| 0.20 | 117.2 |
| 0.50 | 123.0 |
| 0.80 | 127.3 |
| 1.10 | 128.6 |
| 1.40 | 130.3 |
| 1.75 | 130.3 |
| 2.00 | 128.8 |

As can be derived from Table 3 above the extract according to the present invention is stable and maintains its stimulating effect on the cells metabolism, while showing no cytotoxic effect.

As a consequence of the hypothesized anti-oxidative effect and inhibition of endothelin described above or by other unknown additional effects a strong melanin inhibitory effect could be demonstrated, in-vitro as well as in vivo.

In vitro Inhibition of Melanin

Mouse melanoma cells were grown in RPMI 1640 medium supplemented with 10% FCS, L-glutamine and gentamycin. After trypsination $3.5 \times 10^5$ cells/ml were filled in T25 flasks with 8 ml medium. Incubation for 48 hours (37° C., 10% $CO_2$) was followed by removal of medium and carefully washing with 3 ml of phosphate buffer (PBS). *Bellis perennis* extract containing preservatives had to be dialysed (MW cut-off: 500 Da). The samples were diluted in 8ml medium and transferred into T25 flasks. Flasks which only contained medium without sample served as control. The flasks were incubated for 72 hours (37° C., 10% $CO_2$) and the application was repeated and the flasks incubated for another 48 hours. After completion of the incubation the medium was removed and the cells were washed with 3ml PBS. The cells were trypsinized and the cell count was determined for each flasks (homogenous cell suspension). Then the cell pellets were washed with 4 ml PBS, centrifuged at 1100 rpm for 10 min and 2 ml 5% trichloric acid was added to each pellet and mixed well. The centrifugation step was repeated and the supernatant discarded. The melanin was suspended wit 1.3 ml 1N NaOH and the absorbance read at 475 nm.

TABLE 4 in-vitro depigmenting effect on mouse melanoma cells (B16V)

| % extract | % OD 475 nm |
|---|---|
| 0 (control) | 100 |
| 0.50 | 89 |
| 1.00 | 62 |
| 1.60 | 38 |
| 2.00 | 27 |

(Photographic Documentation of Depigmenting Effect see FIG. 1).

The same test was also performed with an extract according to the present invention which had been stored for 5 months at ambient temperatures.

TABLE 5

Determination of stability on mouse melanoma cells (B16V) after 5 months of storage

| % extract | % OD 475 nm |
|---|---|
| 0 (control) | 100 |
| 0.50 | 88 |
| 1.00 | 71 |
| 1.60 | 44 |
| 2.0 | 30 |

In vivo-evaluation of the Depigmenting Effect

Test Design 5 volunteers (from the Philippines; Asian phenotype, age: 19-39) with healthy skin were included in the study.

The trial was carried out by using the inner site of the forearm as test site. Measurements were carried out at a temperature of 20° C.+/−1° C. and a relative humidity of 50%+/−10%.

Volunteers were accustomed to ambient conditions for 30 min prior to the experimental procedures. After the first measurement (Chromameter) the test product and a placebo product (identical to test product but comprising no *Bellis perennis L.* extract) were applied. One field remained untreated and served as control area. The dose of application was about 2 mg/cm$^2$ (application with a Omnifix 1 ml syringe, Braun Melsungen AG, Germany). Measurement were evaluated during treatment on day 14 and 28 about 4 hours after the last daily application. During the 4 weeks period the products were applied twice daily at home. Subjects were instructed not to use any other topical preparations on the test area starting from 3 days prior to the test until after the test. For cleansing, water or a mild syndet (Eubos® flüssig blau) was allowed only.

Measurement

Skin colour was measured with a Minolta Chromameter CR300 (Minolta, Japan) in compliance with the Commission Internationale de l'eclairage (CIE) system, according to which the registration of colour is adjusted to the non-linear colour sensitivity of the human eye. A colour is expressed in a three dimensional coordinate system with green-red (a*), yellow-blue(b*) and L* axes (brightness). The skin surface is illuminated by a Xenon flashlight and remitted light is registered and analysed by a photoreceiver. In whitened skin a positive change on the L* axis is observed. Each value is the average of three recordings. Before each measuring series the instrument was calibrated against the standard white tile. Measurements are according to the guidelines of the Standardisation Group of the European Society of Contact Dermatitis (Fullerton et al., Contact Dermatitis, 1996, 35, 1-10).

Biometry

Measurement data were centrally computerized after validity check and quality assurance. Evaluation was carried out using the software WinSTAT® Add-in for Excel-R. K. Fitch, Germany.

Results

The test formulation according to the invention with 2% *Bellis perennis* extract showed after 2 and 4 weeks of treatment a clear whitening/lightening effect (about 40% reduction of melanin content) in comparison with the untreated area and the area treated with placebo (see FIG. 2). This depigmentation or whitening effect is significantly superior to results that can be achieved with depigmenting or whitening agents of the prior art.

No incompatibility was observed in any of the subjects.

In-vivo Evaluation of Dermatological Acceptance by Repeated Human Patch Test

Test Design

In order to determine any possible skin irritating effects of the formulations according to the invention the repeated human patch test (J. E. Wahlberg: "Patch Testing" in R. J. G. Rycroft, T. Menne', P. J. Frosch and Benezra (eds.), Textbook of Contact Dermatitis, Springer-Verlag, Berlin (1992), p.241-265, p.241-265) was performed with a test formulation comprising 10% (w/w) *Bellis perennis L.* extract which allowed the assessment of the skin irritation potential of the formulation.

The test was performed with 50 volunteers between the age of 18 and 65 having sensitive skin.

The test product was applied undiluted in square test chambers (Haye's Test Chambers; HAL Allergie GmbH, Düsseldorf, Germany) to the back of the test subjects for three weeks (weekly: three times for a period of 24 hours under occlusion). After two weeks, test chambers filled with the product were applied to the same treated area and to an untreated area to test for a possible sensitation. Treatment sites were assessed for the presence of irritation by a trained evaluator using a 5 point visual scoring scale at 24 hours (30 min after patch removal), 48 hours, 72 hours and 96 hours after patch application.

Scoring Scale:
Erythema: 0: no erythema; 1: slight erythema; 2: significant erythema; 3: pronounced erythema; 4: strong erythema
Fissure: 0: no fissure; 1: minimal fissure; 2: significantly perceptible fissure erythema; 3: pronouced fissure; 4: ulceration
Scaling: 0: no scaling; 1: minimal scaling; 2: moderate scaling; 3: significant scaling; 4: closed scale crust Results The test results outlining the data for erythema, fissure formation and scaling are listed in Table 6 below.

No subject showed any reaction or irritation to the test product. On the basis of the test results it can be demonstrated that the compositions according to the present invention do not cause skin irritation and no hint of sensitation could be observed.

TABLE 6

| no | Reactions during the first 3 weeks | Reaction after 5 weeks | | | | | | | | | | |
|---|---|---|---|---|---|---|---|---|---|---|---|---|
| | | after 24 h | | | after 48 h | | | after 72 h | | | after 96 h | | |
| | | E | F | S | E | F | S | E | F | S | E | F | S |
| 1 | 0 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 |
| 3 (E) | 0 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 | 0 |
| 5 | Plaster irritation | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 | 0 |
| 7 | Plaster irritation | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 | 0 | 0 |
| 12 (E) | 0 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 | 0 |
| 14 | 0 | 0 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 | 0 | 0 |
| 16 (E) | 0 | 0 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 | 0 | 0 |
| 19 | 0 | 0 | 0 | 0 | 0 | 0 | 0 | 0 | 0 | 0 | 0 | 0 | 0 |
| 20 | 0 | 0 | 0 | 0 | 0 | 0 | 0 | 0 | 0 | 0 | 0 | 0 | 0 |
| 21 | 0 | 0 | 0 | 0 | 0 | 0 | 0 | 0 | 0 | 0 | 0 | 0 | 0 |
| 22 | 0 | 0 | 0 | 0 | 0 | 0 | 0 | 0 | 0 | 0 | 0 | 0 | 0 |
| 23 (E) | 0 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 | 0 | 0 |
| 27 (E) | 0 | 0 | 0 | 0 | 0 | 0 | 0 | 0 | 0 | 0 | 0 | 0 | 0 |
| 28 | 0 | 0 | 0 | 0 | 0 | 0 | 0 | 0 | 0 | 0 | 0 | 0 | 0 |
| 29 | 0 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 | 0 |
| Sum | | 0 | 0 | 0 | 0 | 0 | 0 | 0 | 0 | 0 | 0 | 0 | 0 |

| Prob. Nr. | Reactions during the first 3 weeks | Reaction after 5 weeks | | | | | | | | | | |
|---|---|---|---|---|---|---|---|---|---|---|---|---|
| | | after 24 h | | | after 48 h | | | after 72 h | | | After 96 h | | |
| | | E | F | S | E | F | S | E | F | S | E | F | S |
| 31 | 0 | 0 | 0 | 0 | 0 | 0 | 0 | 0 | 0 | 0 | 0 | 0 | 0 |
| 32 (E) | Plaster irritation | 0 | 0 | 0 | 0 | 0 | 0 | 0 | 0 | 0 | 0 | 0 | 0 |
| 33 (E) | 0 | 0 | 0 | 0 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | 0 | 0 | 0 |
| 37 | 0 | 0 | 0 | 0 | 0 | 0 | 0 | 0 | 0 | 0 | 0 | 0 | 0 |
| 38 | 0 | 0 | 0 | 0 | 0 | 0 | 0 | 0 | 0 | 0 | 0 | 0 | 0 |
| 39 | 0 | 0 | 0 | 0 | 0 | 0 | 0 | 0 | 0 | 0 | 0 | 0 | 0 |
| 40 (E) | 0 | 0 | 0 | 0 | 0 | 0 | 0 | 0 | 0 | 0 | 0 | 0 | 0 |
| 41 | 0 | 0 | 0 | 0 | 0 | 0 | 0 | 0 | 0 | 0 | 0 | 0 | 0 |
| 42 (E) | 0 | 0 | 0 | 0 | 0 | 0 | 0 | 0 | 0 | 0 | 0 | 0 | 0 |
| 43 | 0 | 0 | 0 | 0 | 0 | 0 | 0 | 0 | 0 | 0 | 0 | 0 | 0 |
| 44 (E) | 0 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 | 0 |
| 47 | Plaster irritation | 0 | 0 | 0 | 0 | 0 | 0 | 0 | 0 | 0 | 0 | 0 | 0 |

TABLE 6-continued

| | | | | | | | | | | | | | |
|---|---|---|---|---|---|---|---|---|---|---|---|---|---|
| 48 | 0 | 0 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 | 0 | 0 |
| Sum | | 0 | 0 | 0 | 0 | 0 | 0 | 0 | 0 | 0 | 0 | 0 | 0 |

A further advantage of the compositions according to the present invention is the fact that, due to the bactericidal and antifungal activity of *Bellis perennis L.*, the addition of as little as 0.2% potassium sorbate was proved to be sufficient in microbiological challenging tests.

The conventionally used depigmenting agents such as arbutin, kojic acid and hydrochinone mainly exhibit their effect by inhibition of tyrosinase. Apart from stabilisation problems its long term use may also lead to dermatological problems.

Thus the present invention provides a depigmenting agent and compositions comprising said depigmenting agent which inhibit the melanin synthesis leading to a quick lightening of the skin while being dermatologically well tolerated.

The invention claimed is:

1. A method for depigmentation of human skin comprising the application of a cosmetic composition to said skin, wherein said composition comprises a depigmenting effective amount of an extract of *Bellis perennis L.*, and wherein high molecular components of the extract of *Bellis perennis L* have been removed to provide an upper MW cut-off of 500 kDa.

2. The method of claim 1, wherein the composition is a cream, an ointment, an emulsion, a tonic, stick, dispersion, a formulation comprising a tenside, a solution or a gel.

3. The method of claim 1, wherein the composition comprises at least one additional depigmentation agent, anti-inflammatory agent or antioxidant.

4. The method of claim 1, wherein the composition comprises about 1% (w/w) to about 10% (w/w) extract of *Bellis perennis L.*

5. The method of claim 1, for the treatment or amelioration of hyperpigmentation selected from pigmented spots, lentigo senilis, freckles, ephelides, post inflammatory hyperpigmentation, pigmented keratosis, melasma and chloasma and hypopigmentation selected from vitiligo, piebaldism and leucoderma due to cicatrisation.

6. The method of claim 1, wherein the composition comprises from about 2% (w/w) to about 5% (w/w) of extract of *Bellis perennis L.*

7. The method of claim 1, wherein the composition comprises about 3% (w/w) of extract of *Bellis perennis L.*

8. The method of claim 1, wherein high molecular components of the extract of *Bellis perennis L* have been removed to provide an upper MW cut-off of 100 kDa.

9. A method for depigmentation of human skin comprising the application of a cosmetic composition to said skin, wherein said composition comprises a depigmenting agent consisting of a depigmenting effective amount of an extract of *Bellis perennis L.*, wherein high molecular components of the extract of *Bellis perennis L* have been removed to provide an upper MW cut-off of 500 kDa.

10. The method of claim 9, wherein the composition is a cream, an ointment, an emulsion, a tonic, stick, dispersion, a formulation comprising a tenside, a solution or a gel.

11. The method of claim 9, wherein the composition comprises about 1% (w/w) to about 10% (w/w) extract of *Bellis perennis L.*

12. The method of claim 9, wherein the composition comprises from about 2% (w/w) to about 5% (w/w) of extract of *Bellis perennis L.*

13. The method of claim 9, wherein the composition comprises about 3% (w/w) of extract of *Bellis perennis L.*

14. The method of claim 9, wherein high molecular components of the extract of *Bellis perennis L* have been removed to provide an upper MW cut-off of 100 kDa.

15. A method for the treatment or amelioration of hyperpigmentation of human skin selected from pigmented spots, lentigo senilis, freckles, ephelides, post inflammatory hyperpigmentation, pigmented keratosis, melasma and chloasma and hypopigmentation selected from vitiligo, piebaldism and leucoderma due to cicatrisation, comprising the application of a cosmetic composition to said skin, wherein said composition comprises a depigmenting agent consisting of a depigmenting effective amount of an extract of *Bellis perennis L.*

* * * * *